United States Patent [19]

Umen

[11] 4,306,063

[45] Dec. 15, 1981

[54] 4-SUBSTITUTED 3,5-MORPHOLINEDIONES

[75] Inventor: Michael J. Umen, Glenside, Pa.

[73] Assignee: McNeil Laboratories, Inc., Fort Washington, Pa.

[21] Appl. No.: 176,304

[22] Filed: Aug. 8, 1980

Related U.S. Application Data

[62] Division of Ser. No. 71,516, Aug. 31, 1979, Pat. No. 4,256,891, which is a division of Ser. No. 904,080, May 8, 1978, Pat. No. 4,197,315, which is a division of Ser. No. 829,117, Aug. 30, 1977, Pat. No. 4,123,538.

[51] Int. Cl.$^3$ ............................................ C07D 413/06
[52] U.S. Cl. ..................................................... 544/130
[58] Field of Search .......................................... 544/130

[56] References Cited

U.S. PATENT DOCUMENTS 3,563,986  2/1971  Frankus et al. ...................... 544/130
3,770,820  11/1973  Ackerman ............................ 544/130

OTHER PUBLICATIONS

Baron et al., Chem. Abstracts, vol. 70 (1969) No. 39781.

*Primary Examiner*—Henry R. Jiles
*Assistant Examiner*—R. W. Ramsuer

[57] ABSTRACT

Novel (2-amino-2-oxoethoxy)acetic acid compounds and antisecretory compositions and methods employing (2-amino-2-oxoethoxy)acetic acid compounds are disclosed. The (2-amino-2-oxoethoxy)acetic acid compounds are also useful as cardiotonic agents and as calcium binding agents; certain of the compounds are also useful for their calcium transport properties. Novel 4-substituted 3,5-morpholinediones intermediates in the preparation of certain of the (2-amino-2-oxoethoxy)acetic acid compounds and further useful as antisecretory agents are also disclosed.

3 Claims, No Drawings

4-SUBSTITUTED 3,5-MORPHOLINEDIONES

This is a division of application Ser. No. 71,516, filed Aug. 31, 1979 (now U.S. Pat. No. 4,256,891), which was a division of application Ser. No. 904,080, filed May 8, 1978 (now U.S. Pat. No. 4,197,315), which was a division of application Ser. No. 829,117 filed Aug. 30, 1977 (now U.S. Pat. No.4,123,538).

BACKGROUND OF THE INVENTION

Certain [2-(substituted-amino)-2-oxoethoxy]acetic acids have been reported previously. The compound having the formula

HOOC—CH$_2$—O—CH$_2$—CONHC$_6$H$_5$ has been reported by Anschutz, Ann., 259, 187 (1890); no pharmacological property is disclosed. Diglycolamic acids in which the nitrogen is substituted with a non-cyclic aliphatic hydrocarbon group have been reported to be useful additives to gasolines as rust and corrosion inhibitors (U.S. Pat. No. 3,183,069). The compound represented by the formula

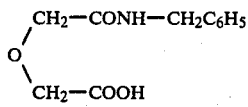

has been described by Baron, et al., J. Med. Chem., 10, 276 (1967), as an intermediate in the preparation of a morpholinedione represented by the formula

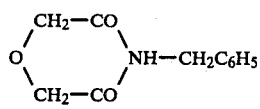

Other morpholinediones disclosed to have been obtained throgh amide acid intermediates are those represented by the formulas

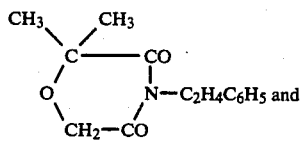

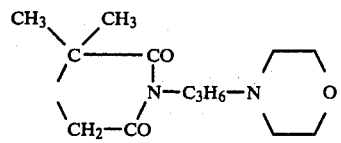

The morpholines have CNS depressant properties. No pharmacological properties are suggested for the amide acid compounds. Of the reported morpholinediones which are N-substituted, there may be mentioned in addition to the aforementioned Baron compounds, compounds more remote in which the substituent on the 4 nitrogen is (a) alkyl and useful as intermediates for the preparation of metal sequestrants (Kidwell et al., Ger. Offen. No. 2,511,613 (South Africa Nos. 75/1646) and U.S. Pat. No. 2,511,888); and as sweetening agents (M. Sido abstracted in J. Chem. Soc. 447(1921)) (b) aralkyl used for investigating hypolipidemic activity; and (c) nitrogen substituted alkylene in which the nitrogen is part of a complx structure which necesarily contains an azo linkage and useful as dyes (M. A. Weaver et al., U.S. Pat. No. 3,699,092). None of the foregoing amide acid compounds or morpholinediones is known to have antisecretory or cardiotonic properties.

SUMMARY OF THE INVENTION

This invention relates to novel (2-amino-2-oxoethoxy)acetic acid compounds, and to novel antisecretory compositions and methods in which the (2-amino-2-oxoethoxy)acetic acid compounds, more particularly the [2-(substituted-amino)-2-oxoethoxy]acetic acids and their salts are the active agents. The novel compounds are also useful as cardiotonic agents and further have calcium binding properties. Certain of the compounds are useful as agents for transporting calcium, particularly for beneficial physiological uses. The invention embraces 4-substituted-3,5-morpholinediones which are intermediates in the preparation of certain of the (2-amino-2-oxoethoxy)acetic acid compounds. These latter compounds also are useful for inhibiting gastric acid secretion.

DESCRIPTION OF THE INVENTION

The novel (2-amino-2-oxoethoxy)acetic acid compounds which are active agents in antisecretory compositions and methods and compounds (a) which may be represented by the formula

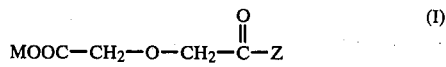

$$MOOC-CH_2-O-CH_2-\overset{O}{\underset{\|}{C}}-Z \qquad (I)$$

or (b) which may be represented by the formula

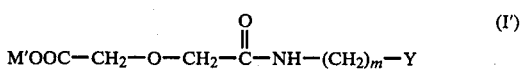

$$M'OOC-CH_2-O-CH_2-\overset{O}{\underset{\|}{C}}-NH-(CH_2)_m-Y \qquad (I')$$

wherein M and M' are hydrogen or a salt cation and Z and Y are nitrogen bearing radicals. The compounds of Formula I' possess a basic nitrogen and are capable of being in the form of zwitterions or internal salts as hereinafter seen. They are also capable of forming acid addition salts with strong acids; these acid addition salts also constitute part of the present invention.

In the foregoing and succeeding formulas,

M is hydrogen, alkali metal, alkaline earth metal, ammonium or substituted ammonium;

M' is hydrogen, alkali metal, alkaline earth metal or quaternary ammonium;

Z is a radical represented by

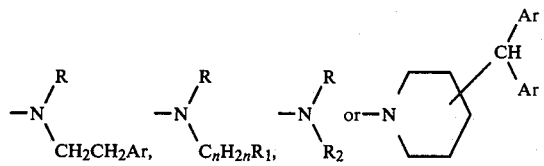

wherein R is hydrogen or lower alkyl; R$_1$ is cycloalkyl containing from 5 to 6 carbon atoms; R$_2$ is cycloalkyl or a di- or tri-condensed cyclalkyl wherein each ring of said condensed cycloalkyl contains from 5 to 6 carbon atoms; each Ar independently is phenyl, trifluoromethylphenyl, or lower alkyl-, lower alkoxy- or halo-substituted-phenyl and n is an integer of from 2 to 3, and Y is a radical represented by

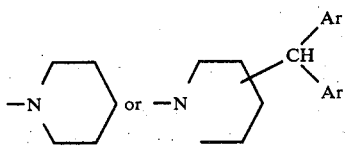

each Ar independently is phenyl, trifluoromethylphenyl, or lower alkyl-, lower alkoxy- or halo-substituted-phenyl.

In the foregoing definitions, the expression "alkali metal" includes lithium, sodium and potassium; the expression "alkaline earth metal" embraces calcium, barium and magnesium; "substituted ammonium" includes lower alkylammonium and lower hydroxyalkylammonium, such as methylammonium, ethylammonium, isopropylammonium, n-butylammonium, 2-hydroxyethylammonium, 2-hydroxypropylammonium, 2-hydroxy-1-methylethylammonium, t-butylammonium, trimethylammonium, tetramethylammonium, 3-hydroxypropylammonium and the like. The expression "lower alkyl" refers to straight and branched chain saturated aliphatic hydrocarbon radicals having from 1 to about 5 carbon atoms such as, for example, methyl, ethyl, isopropyl, pentyl, isoamyl, etc. The expression "quaternary ammonium" includes tetraalkylammonium, preferably, where the alkyl is from 1 to 4 carbon atoms. The expression"cycloalkyl" embraces cyclopentyl and cyclohexyl. The expression "di- or tri-condensed cycloalkyl" embraces such radicals as adamantyl, norbornanyl, bornanyl and the like. The expressions "lower alkyl-substituted phenyl" and "lower alkoxy-substituted phenyl" embraces mono and poly substituted phenyls in which the total carbon supplied by the lower alkyl or lower alkoxy substituent is up to about 5 carbon atoms. It is contemplated that more than one type of substituent may be present on the phenyl nucleus. Representative lower alkoxy-substituted-phenyl and lower alkyl-substituted-phenyl radicals are anisyl, p-ethoxyphenyl, o-ethoxyphenyl, p-isopropoxyphenyl, p-t-butoxyphenyl, p-isoamyloxyphenyl, tolyl, xylyl, mesityl, isoamylphenyl, t-butylphenyl, sec.-propylphenyl, p-isopropyl-o-tolyl, 2,5-dimethylphenyl, and the like. The expression "halo-substituted-phenyl" refers to phenyl substituted with any of the halogen groups including chloro, bromo, fluoro and iodo and which may also contain a lower alkyl or lower alkoxy group. Representative halo-substituted-phenyl radicals are p-bromophenyl, p-chlorophenyl, p-iodophenyl, p-fluorophenyl, o-chlorophenyl, m-chlorophenyl, o-chlorophenyl, m-chlorophenyl, o-fluorophenyl, p-chloro-o-methoxyphenyl, p-bromo-o-methylphenyl, 2,4-dichlorophenyl, 2,4-dichlorophenyl, and the like.

The compounds represented by Formula I' which possess a basic nitrogen group may be in the form of a zwitterion (I'a') when M' is hydrogen as may be seen by the following equilibrium

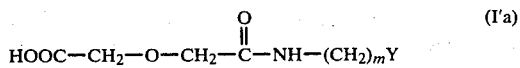

(I'a)

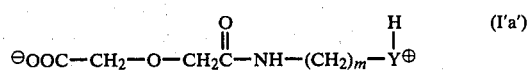

(I'a')

Zwitterions of Formula I'a' may form acid addition salts with strong acids. The acid addition salts may be those of an inorganic or organic acid. Representative inorganic acids include hydrohalic acids, e.g., hydrochloric, hydrobromic or hydriodic acid; sulfuric, nitric acid, or phosphoric acid and the like. Representative organic acids include picric, methanesulfonic, ethanesulfonic, benzenesulfonic, p-toluenesulfonic, naphthalenesulfonic acids and the like. The pharmaceutically acceptable acid addition salts of the compounds of Formulas I' are included within the scope of the present invention.

The novel (2-amino-2-oxoethoxy)acetic acid compounds of the present invention are generally white crystalline solids. The products in acid form are generally soluble in aqueous alkali or a solution of a base in polar solvents; the products in salt form are generally soluble in water or polar solvents. The compounds have valuable pharmacological properties, particularly inhibition of gastric acid secretion and pharmaceutical compositions comprising the novel compounds and methods for inhibiting gastric secretion constitute a part of the present invention. The compounds also have properties of stimulating the heart muscle and are adapted to be employed in cardiotonic compositions. They are useful as cation binding agents and particularly have calcium binding properties which are adapted to be employed to counteract hyperabsorption of calcium or to inhibit anomalous deposition or mobilization of calcium in the body. They are further adaptable to being employed as components in detergent, surfactant, scale removal and the like compositions. Certain of the compounds also have properties suitable for use as agents for the aid of transporting metal, particularly calcium.

The (2-amino-2-oxoethoxy)acetic acid compounds represented by Formula I may be prepared in the following manner. Those compounds in which M is hydrogen (Ia) may be prepared by reacting diglycolic anhydride (II) with an appropriate primary or secondary amine of Formula III, preferably in an appropriate inert organic solvent:

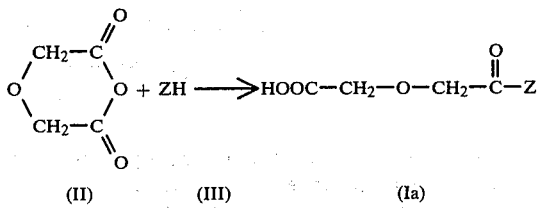

(II)    (III)    (Ia)

For the preparation of a compound of Formula Ia, substantially equimolar amounts of the diglycolic anhydride and amine reactants preferably are employed. Suitable solvents include dimethylformamide; dimethylsulfoxide; halohydrocarbons such as chloroform, dichloromethane, carbon tetrachloride, 1,2-dichloroethane, and the like; ethers, such as diethyl ether, dioxane, tetrahydrofuran, 1,2-dimethoxyethane and the like; aromatic hydrocarbons such as benzene, toluene, xylene, and the like. The reaction may be carried out in the absence of solvent. The temperature of the reaction may be from about 0° C. to the reflux temperature of the solvent, with the range from about 15° to 35° being preferred. The reaction time sufficient to substantially complete the reaction is generally from several minutes to several hours, preferably from about thirty minutes to about two hours.

In carrying out the reaction, the reactants are intimately admixed, preferably by adding portionwise while stirring a solution of diglycolic anhydride in an inert solvent to a solution of the appropriate amine also in an inert solvent, and the mixing continued with or without the application of heat for time sufficient to complete the reaction with the formation of the desired product of Formula Ia in the reaction mixture. The product may be recovered and purified by conventional procedures such as vaporizing the solvent in whole or in part by conventional means and recovering the solid or oil which separates out or remains as residue. The solid may be recrystallized if desired from suitable solvents such as alcohols or esters, e.g., isopropanol, ethyl acetate and the like, or solvent mixtures such as isopropanol-water, ethyl acetate-hexane and the like.

Those compounds of Formula I which are in the salt form (Ib), i.e., M is alkali metal, alkaline earth metal, ammonium or substituted ammonium, may be prepared by intimately contacting the compound in the acid form (Formula Ia) with a substantially equivalent amount of an appropriate base WOH preferably in a solvent and thereafter recovering the salt form (Ib) of the product as residue, e.g., by vaporizing the solvent.

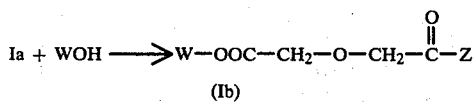

(Ib)

(W represents the salt cation.) The salt may be purified, if desired, employing conventional procedures. Appropriate bases are alkali metal, alkaline earth metal, ammonium and substituted ammonium hydroxides and amines. (WOH as above employed is intended to include amines as sources of substituted ammonium hydroxide to indicate relationship to other bases in the intended function.)

The (2-amino-2-oxoethoxy)acetic acid compounds represented by Formula I′ may be prepared from the appropriate novel 4-(substituted aminoalkyl)-3,5-dioxomorpholinedione of Formula IV (prepared as subsequently described)

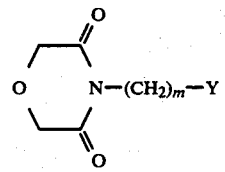

in the following manner: The salt (I′b) may be prepared by intimately admixing IV with substantially one equivalent of a base, UOH, in water or in water in mixture with a watermiscible ethereal solvent and the mixing continued in the temperature range of 20° to 100° C. preferably while gradually increasing temperature and simultaneously reducing the pressure to remove solvent and to produce the novel salt of Formula I′b wherein U is alkali, alkaline earth metal or quaternary ammonium.

The acid (I′a) i.e., M′ is hydrogen, may be prepared by (1) intimately contacting the salt (I′b) with at least one equivalent of a concentrated aqueous base, UOH, in water or a polar solvent at reflux temperature to produce a diamine of Formula V (and diglycolic acid salt) and isolating the diamine by extracting into a water-immiscible, inert organic solvent and (2) thereafter reacting the diamine (V) with a substantially equivalent amount of diglycolic anhydride (II) either in an inert organic solvent or neat. The conditions suitable for this latter step is as described for the reaction between diglycolic anhydride and amine in the preparation of Ia. The acid (I′a) may be purified also as described for the acid (Ia). Alternatively, in the preparation of the acid (I′a), the diamine (V) may be obtained directly from the morpholinedione of Formula IV by employing at least two equivalents of UOH. The foregoing may be seen in the following diagram:

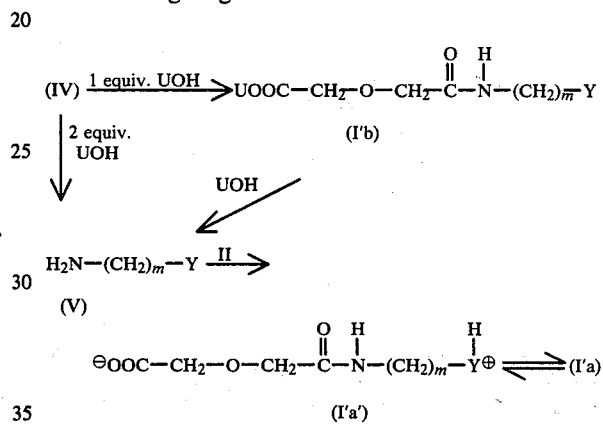

The acid addition salt (I′c) of I′

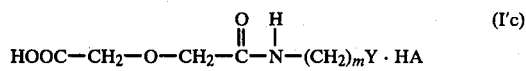

wherein HA represents a strong acid as hereinbefore defined, may be obtained by adding one equivalent of an acid HA, to the salt (I′a) and thereafter after purifying, if desired, by conventional procedures.

The intermediate 4-(substituted-aminoalkyl)-3,5-morpholinedione of Formula IV in addition to being useful intermediates for the preparation of the compounds of Formula I′ have valuable properties adaptable to being employed as active components of antisecretory agents and these compounds constitute an aspect of the present invention.

The compounds of Formula IV may be prepared by a sequence of reactions comprising (1) reacting diglycolic anhydride (II) with an appropriate aminoalkanol (VI) to produce a [2-hydroxyalkylamino-2-oxoethoxy]acetic acid (VII); (2) heating the acid to produce 4-hydroxyalkyl-3,5-morpholinedione (VIII); (3) reacting the morpholinedione thus produced at the hydroxy group with a reagent which substitutes the hydroxy group with displaceable group, "D" to produce the appropriately substituted morpholinedione derivative (IX); and reacting the latter compound with a suitable amine, YH (X). Preferred aminoalkanols are ω-aminoalkanols such as 6-amino-n-hexanol, 4-amino-n-butanol, 2-aminoethanol, 3-aminopropanol, etc.

The displaceable group D may be a halide or an active ester group such as —O—tosyl, —O—mesyl and the like. The reactions may be represented by the following schematic diagram:

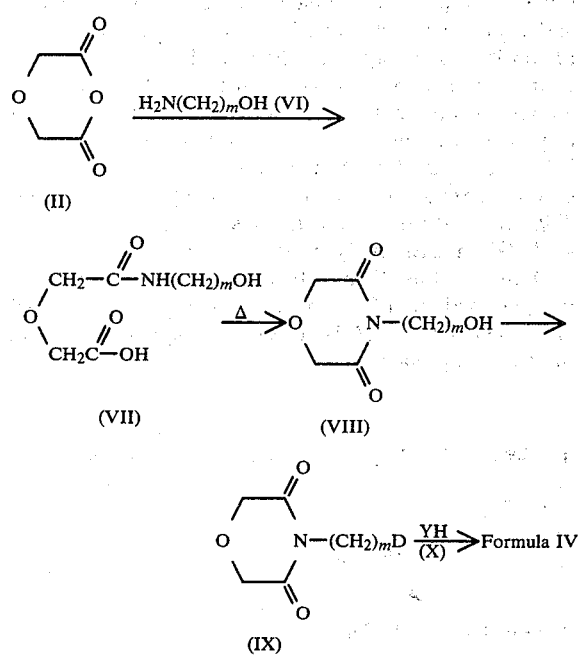

In carrying out the preparation, the first step is carried out by intimately admixing diglycolic anhydride and aminoalkanol in a solvent such as those employed in the preparation of the compound of Formula Ia previously described. Substantially equimolar amounts of the reactants are employed. The reaction temperature is within the range of from about 0° C. to reflux temperature of the solvent and the reaction time from several minutes to several hours with the preferred conditions being from about 15° to about 35° C. for about 30 minutes to two hours. After completion of the reaction, the solvent is removed from the reaction mixture by vaporization and the residue is heated under reduced pressure as the second step to remove the water and to cyclize the amide acid intermediate to the compound of Formula VIII. The heating step is carried out for time sufficient to complete the cyclization and the removal of the water. The preferred conditions are temperatures in the range from about 200° to 230° C. and pressures of about 18-22 torricelli for a period of from about 1 to 3 hours. The 4-(hydroxyalkyl)-3,5-morpholinedione of Formula VIII may be recovered in substantially pure form by distillation.

The third step is carried out by adding to a solution of the 4-(hydroxyalkyl)-3,5-morpholinedione thus obtained, a substantially equimolar proportion of a reagent producing a halide or active ester group in a portionwise manner and with cooling to produce the compound of Formula IX. Suitable solvents for carrying out the reaction include pyridine, collidine, picoline, and inert solvents such as dioxane, tetrahydrofuran, 1,2-dimethoxyethane, diethyl ether, chloroform, dichloromethane, toluene, etc., usually with added basic reagents such as trimethylamine, sodium carbonate, etc. Suitable reagents for providing the displaceable group include tosyl chloride, mesyl chloride, thionyl chloride and the like. The temperature for the reaction is in the range of from about 0° to about 20° C. The morpholine derivative (IX) may then be recovered and purified, if desired, by conventional procedures.

In the fourth step, the compound of Formula IX is then reacted with a substantially equimolar amount of an appropriate amine, YH, to produce the desired intermediate morpholinedione compound of Formula IV. The reaction between the compound of Formula IX and the amine, YH, employs the conditions which are amply described in the literature. The reaction may be carried out in an inert liquid reaction medium at temperatures of from about 60° C. to about 200° C. in the presence or absence of a base suitable for use as an acid binding agent. Lithium hydride is a particularly preferred acid binding agent but other inorganic and tertiary organic bases may be employed including other alkali metal and alkaline earth metal hydrides, and tertiary amines. Suitable reaction periods range from about 2 hours to about 4 days for satisfactory yields. Suitable solvents for reaction media include dimethylformamide; ethereal solvents such as tetrahydrofuran, 1,2-dimethoxyethane, dioxane; secondary or tertiary alcohols such as isopropanol, t-butanol, etc. After completion of the reaction, if carried out in the absence of base, the 4-(substituted amino)-3,5-morpholinedione product (IV) is obtained as an acid addition salt which may be recovered by filtration or volatilization of the solvent. The product may be purified by conventional procedures. If the reaction is carried out in the presence of base, the product (IV) is obtained as a free base and may be recovered by filtration and subsequent volatilization of the solvent from the filtrate. The product may be purified, if desired, by distillation, crystallization or formation of an acid addition salt. Typical acids for forming acid addition salts include inorganic acids such as hydrochloric, hydrobromic, hydroiodic, phosphoric, nitric and the like acids, or organic acids such as acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicyclic and the like acids.

The desired antisecretory properties of the (2-amino-2-oxoethoxy)acetic acid compounds of Formulas I and I', including the acid addition salts (I'c) of the compounds of Formula I', and the morpholinediones of Formula IV, and their acid addition salts may be demonstrated with the acute gastric fistula rat test. In the test, determinations for antisecretory activity is carried out in female Sprague-Dawley rats after intraduodenal (i.d.) injection of the compound at doses generally ranging from 2.5-80 mg/kg. body weight. The rats are fasted 24 hours before testing and are given water ad libitum while being kept in individual cages. On the day of testing, the rats are weighed and are selected so that the rats in each test have weights within a range of ±20 grams.

Surgery for the acute gastric fistula test is carried out under light ether anesthesia. As soon as the rat is anesthetized, its teeth are removed using a small pinch pliers. A mid-line incision is made on the abdomen about 1½ centimeters in length and the stomach and duodenum are exposed. If at this point, the stomach is filled with food or fecal material, the rat is discarded. Using 4-0 suture, a purse string stitch is placed on the fundic portion of the stomach taking care not to pierce any blood vessels in the area. A small nick is made into the stomach in the center of the purse string, and a cannula, consisting of a small vinyl tube with a flange on one end, is put into the stomach and the purse string stitch is closed tightly around the flange. Immediately following this, the test compound is administered I.D. in a volume of 0.5 milliliter per 100 gram rat. Three rats are generally used for each drug dose tested. Control rats receive the test vehicle, usually 0.5 percent aqueous methyl cellulose.

After administration of the test compound, the abdominal wall and skin are closed simultaneously with three to four 18 millimeter wound clips and a collecting tube is place on the cannula. Each rat is then placed in a box in which a longitudinal slit has been made to allow the cannula to hang freely and to allow the rat to move about unencumbered. After the rat is allowed to stabilize for 30 minutes, the collection tube on the cannula is discarded and replaced with a clean tube to receive the gastric juice. Collections are made at one hour. At the end of the study, the cannula is removed and the rat is sacrificed.

The sample of gastric contents collected is drained into a centrifuge tube and centrifuged to pack down the sediment. Volumes are read and a 1 milliliter aliquot of the supernatant is put into a beaker containing 10 milliliters of distilled water and is titrated to pH 7 using 0.01 N NaOH. Results are determined for Volume, Titratable Acid, and Total Acid Output where Volume=total milliliter of gastric juice minus sediment; Tritratable Acid (milliequivalents/liter)=amount of 0.01 N NaOH needed to titrate the acid to pH 7; and Total Acid Output=Titratable Acid×Volume. Results are reported in Percent Inhibition vs. Controls and a minimum of 5 percent Inhibition indicates antisecretory activity.

The (2-amino-2-oxoethoxy)acetic acid compounds and morpholinedione compounds show antisecretory properties on administration at doses in the range of from about 2.5 mg/kg to 80 mg/kg of body weight. In representative tests carried out as above-described with {2-[(2-cyclohexyl-1-methylethyl)methylamino]-2-oxoethoxy}acetic acid, [2-(1-adamantylamino)-2-oxoethoxy]acetic acid, [2-oxo-2-(2-phenethylamino)ethoxy]acetic acid, [2-oxo-2-(methyl-2-phenethyl)aminoethoxy]acetic acid, sodium {2-[N-(6-piperidinohexyl)]amino-2-oxoethoxy}acetate, and with 4-(6-piperidinohexyl)-3,5-dioxomorpholine.p-toluenesulfonate and readings made one hour after administration, valuable antisecretory activities were observed with readings of 64 percent, 79 percent, 35 percent, 68 percent, 91 percent and 82 percent, respectively. The foregoing results are merely representative and it is not intended to limit the scope of the pharmacologically desirable properties of the (2-amino-2-oxoethoxy)acetic acid compounds and morpholinedione compounds.

The amide acid compounds are also active in cardiotonic screening tests and are adapted to be employed as active ingredients in compositions suitable as heart stimulants. The desired properties may be demonstrated in the papillary muscle test, similar to that described by H. G. Schoepke et al., J. Pharm. Exp. Ther. 133, 171 (1961). Briefly, in this test the papillary muscle is removed from the right ventricle of a cat's heart and held immersed by a plastic holder in a tissue chamber containing 30 milliliters of a Krebs-Hensleit solution maintained at a constant temperature of 38° C. and aerated with a mixture of 95 percent oxygen and 5 percent carbon dioxide. The muscle is stimulated to contract by means of a square wave stimulator. Drugs are added to the bath and responses are calculated as percent changes relative to the amplitude existing just prior to addition of the drug. Ouabain 1 microgram/milliliter was used as a positive control. Any compound producing a stimulation of 25 percent or greater is considered to be active.

In representative tests carried out with {2-[(2-cyclohexyl-1-methylethyl)methylamino]-2-oxoethoxy}acetic acid, [2-(1-adamantylamino)-2-oxoethoxy]acetic acid, [2-oxo-2-(2-phenethylamino)ethoxy]acetic acid, [2-oxo-2-(methyl-2-phenethyl)aminoethoxy]acetic acid, sodium {2-[N-(6-piperidinohexyl)]amino-2-oxoethoxy}acetate, and with 4-(6-piperidinohexyl)-3,5-dioxomorpholine.p-toluenesulfonate at a concentration of 100 micrograms per milliliter, the compounds were found to be active.

In view of the aforementioned antisecretory activities of the (2-amino-2-oxoethoxy)acetic acid compounds (I and I') and the pharmaceutically acceptable acid addition salt of I', as well as the cardiotonic activities of the compounds, this invention provides valuable methods and compositions comprising the said compounds as the active ingredient in a pharmaceutically acceptable solvent or carrier and, in addition, it provides an effective method of inhibiting gastric secretion To prepare the pharmaceutical compositions of this invention, a (2-amino-2-oxoethoxy)acetic acid compound (I or I') or the pharmaceutically acceptable acid addition salt of I' as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 micrograms of the active ingredient, preferably, from about 10 to about 250 micrograms.

The foregoing compositions are particularly suitable for use in inhibiting gastric acid secretion by a method comprising internally administering to a gastric hyperacidic subject compositions comprising an effective gastric acid secretion inhibiting amount of a (2-amino-2-oxoethoxy)acetic acid compound. The compositions are also suitable for use as cardiac stimulant by a method comprising internally administering compositions comprising an effective cardiac stimulating amount of a compound of Formula I or I' or a pharmaceutically acceptable acid addition salt of I'.

The following examples illustrate the invention but are not construed as limiting.

EXAMPLE I

{2-[(2-Cyclohexyl-1-methylethyl)methylamino]-2-oxoethoxy}-acetic Acid

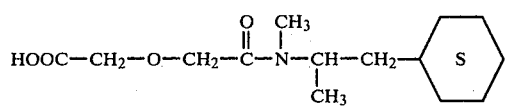

A solution of 11.63 grams (0.100 mole) of diglycolic anhydride in 1 liter of dichloromethane (prepared by heating the anhydride and dichloromethane on a steam bath) was added to a solution of 15.55 grams (0.100 mole) of propylhexedrine in 700 milliliters of dichloromethane at temperatures in the range of from about 21° to about 30° during an interval of about 10 minutes. After the addition, the mixture was stirred at a temperature range of 25° to 30° C. for about 40 minutes whereupon a reaction took place with the formation of a product in the reaction mixture. The mixture was then concentrated on a rotary evaporator to recover the {2-[(2-cyclohexyl-1-methylethyl)methylamino]-2-oxoethoxy}-acetic acid product as a partially crystalline residue which after recrystallization from an ethyl acetate-hexane mixture was in the form of white plates, m.p. 90°–91° C.

Anal. Calcd. for $C_{14}H_{25}NO_4$: C, 61.96; H, 9.29; N, 5.16.

Found: C, 61.98; H, 9.29; N, 5.21.

EXAMPLE II

[2-(1-Adamantylamino)-2-oxoethoxy]acetic Acid

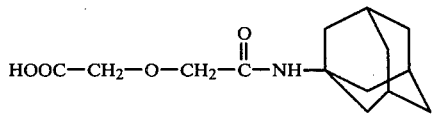

In a similar operation, a solution of 11.56 g (0.100 mole) of diglycolic anhydride in 1 liter of dichloromethane was added with stirring to a solution of 15.11 grams (0.100 mole) of 1-adamantanamine in 700 milliliters of dichloromethane during about 24 minutes at about 15° to 25° C., whereupon a reaction took place with the formation of heterogeneous milky white mixture. The mixture was stirred for 3.67 hours at temperatures of about 23°–25° C. to complete the reaction with the formation of the desired product in the reaction mixture. The mixture was then concentrated on a rotary evaporator to recover 32.7 grams of a white solid which after recrystallization from 1:1 isopropanol-water mixture yielded the desired [2-(1-adamantylamino)-2-oxoethoxy]acetic acid as white plates, m.p. 181°–183° C.

Anal. Calcd. for: $C_{14}H_{21}NO_4$: C, 62.90, H, 7.92; N, 5.24.

Found: C, 62.89, H, 7.94; N, 5.27.

EXAMPLE III

[2-Oxo-2-(2-phenethylamino)ethoxy]acetic Acid

In a manner similar to that described in the Examples I and II, a warm solution of 11.60 grams (0.100 mole) of diglycolic anhydride in 1 liter of dichloromethane was added to a solution of 12.05 grams (0.100) mole of phenethylamine in 700 milliliters of dichloromethane. The mixture was stirred for about 1.7 hours at a temperature in the range of 22° to 28° C. to obtain the desired product which remained in the reaction mixture. After concentrating the mixture and recrystallizing from ethyl acetate, 13.94 grams of purified [2-oxo-2-(2-phenethylamino)ethoxy]acetic acid product was obtained as snow white needles, m.p. 105°–106.5° C.

Anal. Calcd. for: $C_{12}H_{15}NO_4$: C, 60.75; H, 6.37; N, 5.90. Found: C, 60.76; H, 6.37; N, 5.90.

EXAMPLE IV

[2-Oxo-2-(methyl-2-phenethylamino)ethoxy]acetic Acid

In a similar manner, to a solution of 13.48 grams (0.100 mole) of N-methylphenethylamine in 700 milliliters of dichloromethane was added a solution of 11.56 grams (0.100 mole) of diglycolic anhydride in 1 liter of dichloromethane over a period of 12 minutes and thereafter stirred for about 1 hour at temperatures in the range of about 23° to about 30° C. to obtain the desired product which remained in solution in the reaction mixture. At the end of this period, the solvent was evaporated to obtain a yellow oil; the latter was dispersed in hot water and allowed to crystallize to obtain a purified [2-oxo-2-(methyl-2-phenethylamino)ethoxy]-acetic acid product as white needles, m.p. 71°–73° C.

Anal. Calcd. for: $C_{13}H_{17}NO_4$; C, 62.14; H, 6.82; N, 5.57. Found: C, 62.06; H, 6.87; N, 5.61.

EXAMPLE V

[2-(4-Benzhydrylpiperidino)-2-oxoethoxy]acetic Acid

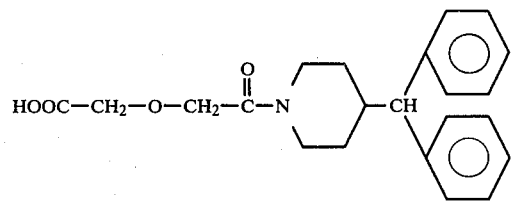

In a similar operation, 5.0 grams (20 millimoles) of 4-benzhydrylpiperidine in 140 milliliters of dichloromethane was reacted with 2.3 grams (20 millimoles) of diglycolic anhydride in 200 milliliters of dichloromethan to obtain the desired [2-(4-benzhydrylpiperidino)-2-oxoethoxy]acetic acid product as white solid which after purifying with ethyl acetate-hexane mixture had a m.p. of 139.5°–141° C.

Anal. Calcd. for: $C_{22}H_{25}NO_4$: C, 71.91, H, 6.86; N, 3.81. Found: C, 71.91; H, 6.90; N, 3.83.

EXAMPLE VI

In operation similar to that described in Example I, the following compounds may be prepared:

{2-[2-cyclopentyl-1-methylethyl)methylamino]-2-oxoethoxy}-acetic acid, from diglycolic anhydride and N,α-Dimethyl-cyclopentaneethanamine.

{2-[(2-cyclohexylethyl)ethylamino]-2-oxoethoxy}-acetic acid, from diglycolic anhydride and N-ethyl-cyclohexaneethanamine.

(2-cyclohexylethylamino-2-oxoethoxy)acetic acid, from diglycolic anhydride and cyclohexaneethanamine.

{2-[(2-cyclopentylethyl)propylamino]-2-oxoethoxy}-acetic acid, from digycolic anhydride and N-propylcyclopentaneethanamine.

{2-[(2-cyclopentylethyl)3-methylbutylamino]-2-oxoethoxy}-acetic acid, from diglycolic anhydride and N-(2-cyclopentylethyl)-3-methylbutanamine.

EXAMPLE VIII

In a manner similar to that described in Example II, the following compounds may be prepared:

[2-(2-Norbornanylamino)-2-oxoethoxy]acetic acid, by the reaction of diglycolic anhydride and 2-norbornanamine.

[2-(2-Bornanylamino)-2-oxoethoxy]acetic acid, by the reaction of diglycolic anhydride and 2-bornanamine.

EXAMPLE VIII

In a manner similar to that described in Example V, the following compounds may be prepared:

{2-[4-Di(p-tolyl)methylpiperidino]-2-oxoethoxy}-acetic acid, by the reaction of 4-di(p-tolyl)methylpiperidine and diglycolic anhydride.

{2-[4-Di(p-cumyl)methylpiperidino]-2-oxoethoxy}-acetic acid, by the reaction of 4-di(cumyl)methylpiperidine and diglycolic anhydride.

{2-[4-Bis(p-isopropoxyphenyl)methylpiperidino]-2-oxoethoxy}acetic acid, by the reaction of 4-bis(p-isopropoxyphenyl)methylpiperidine and diglycolic anhydride.

{2-[4-Di-p-anisyl)methylpiperidino]-2-oxoethoxy}-acetic acid, by the reaction of 4-di(p-anisyl)methylpiperidine and diglycolic anhydride.

{2-[2-Benzhydrylpiperidino]-2-oxoethoxy}acetic acid by the reaction of 2-benzhydrylpiperidine and diglycolic anhydride.

{2-[3-Benzhydrylpiperidino]-2-oxoethoxy}acetic acid by the reaction of 3-benzhydrylpiperidine and diglycolic anhydride.

{2-[4-Bis(3-chloro-p-tolyl)methylpiperidono]-2-oxoethoxy}-acetic acid by the reaction of 4-bis(3-chloro-p-tolyl)methylpiperidine and diglycolic anhydride.

{2-[4-Bis(2-chloro-p-anisyl)methylpiperidino]-2-oxoethoxy}-acetic acid by the reaction of 4-bis(2-chloro-p-anisyl)-methylpiperidine and diglycolic anhydride.

{2-[4-Bis(p-t-butylphenyl)methylpiperidino]-2-oxoethoxy}-acetic acid by the reaction of 4-bis(p-t-butylphenyl)methylpiperidine and diglycolic anhydride.

{2-[4-Bis(p-isoamylphenyl)methylpiperidino]-2-oxoethoxy}-acetic acid by the reaction of 4-bis(p-isoamylphenyl)methylpiperidine and diglycolic anhydride.

{2-[4-Bis-2-chloro-p-tolyl)methylpiperidino]-2-oxoethoxy]-acetic acid by the reaction of 4-bis(2-chloro-p-tolyl)methylpiperidine and diglycolic anhydride.

EXAMPLE IX 4-(6-Piperidinohexyl)-3,5-dioxomorpholine.p-Toluenesulfonate

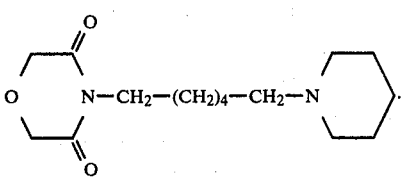

[2-(6-Hydroxyhexyl)amino-2-oxoethoxy]acetic acid

To a solution of 58.5 grams (0.500 mole) of 6-aminohexanol in 3.5 liters of dichloromethane was added in the temperature range of from 20° to 28° C. during about 12 minutes, a warm solution of 58.0 grams (0.500 mole) of diglycolic anhydride in 5.0–5.2 liters of dichloromethane; the addition produced a cloudy mixture with oil depositing on the vessel wall. The mixture was stirred at 25°±3° C. for about one hour; thereafter, the reaction mixture, which contained an insoluble white solid, was filtered to obtain 106.3 grams (91 percent yield) of an off-white solid having appropriate infrared and nuclear magnetic resonance spectra for the [2-(6-hydroxyhexyl)amino-2-oxoethoxy]acetic acid intermediate.

4-(6-Hydroxyhexyl)-3,5-dioxomorpholine 96.3 grams (0.413 mole) of the crude[2-(6-hydroxyhexyl)amino-2-oxoethoxy]-acetic acid was heated to 220° C. to melt the solid; thereafter, the resulting liquid was heated at 220°±10° C. (20±5 torr.) for about 1.5 hours to remove the water and to cause cyclization to occur. The product as a result of these operations was a viscous oil which was distilled to obtain 74.4 grams (84 percent yield) of a purified 4-(6-hydroxyhexyl)-3,5-dioxomorpholine intermediate as a viscous yellow oil having the appropriate infrared and nuclear magnetic resonance 6-(3,5-Dioxomorpholino)hexyl p-toluenesulfonate To 55.5 grams (0.258 mole) of 4-(6-hydroxyhexyl)-3,5-dioxomorpholine was added 82 milliliters of pyridine to obtain a yellow solution. The solution was cooled to 3° C. and to it was added with stirring during about 20 minutes at from 3° to 15° C., 49.2 grams (0.258 mole) of p-toluenesulfonyl (tosyl) chloride. After completion of the addition, stirring was continued at a temperature in the range of from 0° to 7° C. for about 1.5 hours to complete the formation of 6-(3,5-dioxomorpholino)hexyl p-toluenesulfonate intermediate in the reaction mixture. Thereafter, the reaction mixture was poured into a mixture of 157 milliliters of concentrated hydrochloric acid and about 1 liter of ice. The resulting mixture then was extracted with 1500 milliliters of dichloromethane and the resulting dichloromethane solution washed successively with 500 milliliters portions of 1 N aqueous hydrochloric acid, water and saturated aqueous sodium bicarbonate and finally with 250 milliliters of water. The washed solution was dried over magnesium sulfate and concentrated to recover the crude 6-(3,5-dioxomorpholino)hexyl p-toluenesulfonate intermediate as an amber oil in the amount of 83.7 grams (88 percent yield). The intermediate tosylate product has infrared and nuclear magnetic resonance spectral characteristics suitable for the tosylate intermediate.

4-(6-piperidinohexyl)-3,5-dioxomorpholine·p-toluenesulfonate

To a solution of 19.6 grams (53.2 millimoles) of 6-(3,5-dioxomorpholino)hexyl p-toluenesulfonate in 54 milliliters of tertiary butyl alcohol was added 5.3 milliliters of tertiary (53 millimoles) of piperidine in 54 milliliters of tertiary butyl alcohol. The reaction mixture was heated at reflux temperature for about 22 hours to obtain 4-(6-piperidinohexyl)-3,5-dioxomorpholine·p-toluenesulfonate product which crystallized from tertiary butyl alcohol-ether mixture in a yield of 13.45 grams (56 percent) as an off-white solid, m.p. 125°–128° C. A portion of this product after purification by (a) chromatographing on Silicar CC4 Special (Silica gel, product of Mallinkrodt) employing 10:1 dichlormethanemethanol as eluant, (b) recovering from the effluent and (c) recrystallizing from tertiary butyl aclohol-ether, was a white solid, m.p. 121°–122.5° C.

Anal. Calcd. for: $C_{22}H_{34}N_2O_6S$: C, 58.13, H, 7.54; N, 6.16. Found: C, 58.15, H, 7.55; N, 6.18.

From another similar experiment, a higher melting crystalline form of the product, m.p. 130°–131° C. was isolated by crystallization and without chromatography. The two different melting solids were identified as different crystalline forms of 4-(6-piperidinohexyl)-3,5-dioxomorpholine·p-toluenesulfonate by infrared and neclear magnetic resonance spectra, and by interconversion of the lower melting, 121°–122.5° C., solid to a higher melting, 130°–130.5° C., solid on melting, cooling and seeding with the higher melting solid.

EXAMPLE X

Sodium [2-(6-piperidinohexyl)amino-2-oxoethoxy]acetate

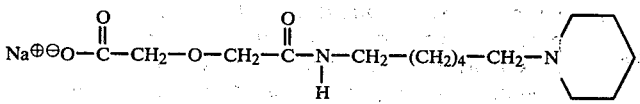

To a mixture of 3.63 grams (9.84 millimoles) of 6-(3,5-dioxomorpholino)hexyl p-toluenesulfonate (prepared as described in Example IX) and 84.75 milligrams (10.7 millimoles) of lithium hydride in 10 milliliters of 1,2-dimethoxyethane was added 1.0 milliliter (10.0 millimoles) of piperidine in 10 milliliters of 1,2-dimethoxyethane. The mixture was heated under reflux for 22 hours, and the resulting heterogeneous mixture filtered to obtain a clear yellow filtrate. The filtrate was concentrated to an orange oil which after evaporation distillation (bath 120° C.; 0.05 torr.) produced 1.18 grams (42.5 percent yield) of 4-(6-piperidinohexyl)-3,5-dioxomorpholine base having infrared and nuclear magnetic resonance spectral characteristics appropriate for said compound. A 286.23 milligram (1.02 millimoles) sample of the free base, 4-(6-piperidinohexyl)-3,5-dioxomorpholine, was dissolved in 1.0 milliliter of 1 N sodium hydroxide (1.0 millimole) and the mixture concentrated to produce 289.63 grams (90 percent yield) of sodium [2-(6-piperidinohexyl)-amino-2-oxoethoxy]acetate product with the following spectral characteristics: IR: (CHCl$_3$); 3700–3150 cm$^{-1}$ (broad); 2935 cm$^{-1}$ 2850 cm$^{-1}$ (shoulder); 1660, 1610 cm$^{-1}$ (broad); 1550 cm$^{-1}$ (shoulder); 1420 cm$^{-1}$ (broad); 1145 cm$^{-1}$; 1120 cm$^{-1}$.

NMR: (D$_2$O; 90 MHz): δ=1.0–2.0 (14H, m, aliphatic —CH$_2$—) 2.11–2.66 (6H, m, —C$\underline{H}_2$-N); 3.06–3.39 (2H, broad t,

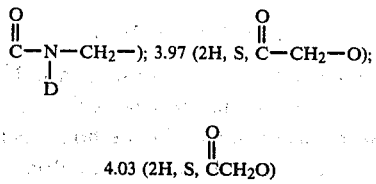

4.03 (2H, S, CCH$_2$O)

EXAMPLE XI

Sodium [2-(6-Piperidinohexyl)amino-2-oxo-ethoxy]acetate

Preparation in situ from 4-(6-piperidinohexyl)-3,5-dioxomopholine·p-toluenesulfonate 43 milligrams (0.095 millimole) of 4-(6-piperidinohexyl)-3,5-dioxomorpholine·p-toluenesulfonate (prepared as described in Example IX) was dissolved in 2 milliliters of 0.1 N sodium hydroxide (0.2 millimole) to obtain an aqueous solution of sodium [2-(6-piperidinohexyl)amino-2-oxoethoxy]acetate and sodium tosylate. The solution had the following spectral characteristics:

NMR: (90 MHz; D$_2$O): δ=1.77–1.18 (14H, m, aliphatic CH$_2$); 2.5–2.03 (6H, m); 2.50 (3H, S, ArC$\underline{H}_3$);

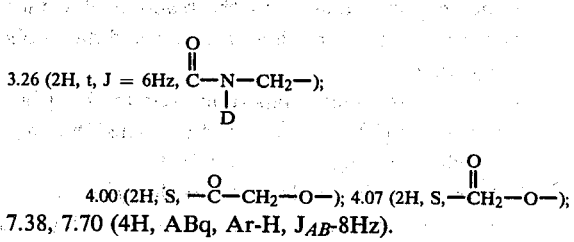

7.38, 7.70 (4H, ABq, Ar-H, J$_{AB}$-8Hz).

EXAMPLE XII

4-[6-(4-Benzhydrylpiperidino)hexyl]-3,5-dioxomorpholine·p-Toluenesulfonate

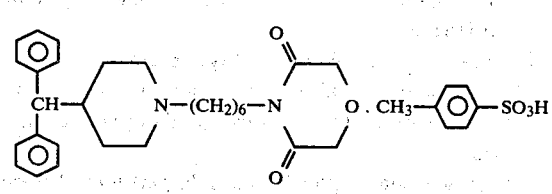

To a solution of 9.75 grams (26.39 millimoles) of 6-(3,5-dioxomorpholino)hexyl p-toluenesulfonate (prepared as described in Example IX) in 160 milliliters of warm tertiary butyl alcohol was added portionwise at temperatures in the range of 30°–32° C. over a period of about 23 minutes, 63 grams (26.38 millimoles) of 4-benzhydrylpiperidine in 160 milliliters of tertiary-butyl alcohol. The reaction mixture was heated at reflux temperature for about 22 hours and thereafter the solvent removed by vaporization to obtain 17.7 grams of a 4-[6-(4-benzhydrylpiperidino)hexyl]-3,5-dioxomorpholine product as a yellow oil. Crystallization (twice) from ethyl acetate produced 4.19 grams of white crystals, m.p., 121°-124.5° C. and having NMR, UV and IR spectral characteristics appropriate for the product.

Anal. Calcd. for $C_{35}H_{44}N_2O_6S$: C, 67.72; H, 7.14; N, 4.51; S, 5.16. Found: C 67.28; H, 7.19; N, 4.57; S, 5.01.

EXAMPLE XIII

Sodium {2-[6-(4-benzhydrylpiperidino)hexyl]amino-2-oxoethoxy}acetate

To 51.70 milligrams of neat 4-[6-(4-benzhydrylpiperidino)hexyl]-3,5-dioxomorpholine which had been prepared by concentrating a NaOH washed dichloromethane solution of the tosylate salt (the salt having been prepared as described in Example XII), was added 1.15 milliliters of 0.1 N aqueous sodium hydroxide and enough tetrahydrofuran to produce a clear yellow solution. The resulting solution was concentrated on a rotary evaporator to obtain the desired sodium salt of {2-[6-(4-benzhydrylpiperidino)hexyl]amino-2-oxoethoxy}acetate as a yellow oil which showed spectral characteristics as follows: NMR (60 MHz, DMSO-$d_6$/$D_2O$): two singlets at $\delta$ 3.85 and 3.95, characteristic of a diglycolamate structure and a broad aromatic singlet at $\delta$ 7.27.

In a further similar experiment, the desired sodium salt was obtained as a thick yellow gum with $R_f$ of 0.6 on silica gel GF 5:1 chloroform-methanol as eluant (distinguishable from $R_f$ 0.8 for imide). Lyophilization of the gum gave a hygroscopic, fluffy white solid.

EXAMPLE XIV 6-(3,5-Dioxomorpholino)hexyl p-toluenesulfonate is prepared as described in Example IX.

Employing procedures similar to that described in Examples IX and XII, the following compounds are prepared as their p-toluenesulfonate salt:

4-{6-[4-Di(p-tolyl)methyl)piperidino]hexyl}-3,5-dioxomorpholine.p-toluenesulfonate by the reaction of 6-(3,5-dioxomorpholino)hexyl p-toluenesulfonate and 4-[di-(p-tolyl)methyl]piperidine.

4-{6-[4-Bis(p-methoxyphenyl)methyl)piperidino]hexyl}-3,5-dioxomorpholine.p-toluenesulfonate by the reaction of 6-(3,5-dioxomorpholino)hexyl p-toluenesulfonate and 4-[bis(p-methoxyphenyl)methyl]piperidine.

4-{6-[4-Bis(p-chlorophenyl)methyl)piperidino]hexyl}-3,5-dioxomorpholine.p-toluenesulfonate by the reaction of 6-(3,5-dioxomorpholino)hexyl p-toluenesulfonate and 4-[bis(p-chlorophenyl)methyl]piperidine.

EXAMPLE XV

Employing procedures similar to that described in Example X or in Example XII taken with Example XIII, the following salts are prepared:

Potassium {2-[6-(4-di(p-tolyl)methyl)piperidino)hexyl]-amino-2-oxoethoxy}acetate by the reaction of 4-{6-[4-di(p-tolylmethyl)piperidino]hexyl}-3,5-dioxomorpholine and potassium hydroxide.

Tetramethyl)ammonium 2-[6-(4-bis(p-methoxyphenyl)methyl)-piperidino)hexyl]amino-2-oxoethoxy acetate by the reaction of 4-{6-[4-bis(p-methoxyphenyl)methyl)piperidino]hexyl}-3,5-dioxomorpholine and tetramethylammonium hydroxide.

Magnesium 2-[6-(4-(bis(p-chlorophenyl)methyl)-piperidino)-hexyl]amino-2-oxoethoxy acetate by the reaction of 4-{6-[4-(bis(p-chlorophenyl)methyl)-piperidino]hexyl}-3,5-dioxomorpholine and magnesium hydroxide.

EXAMPLE XVI

In operations carried out in a manner similar to that described in Examples IX and XIV, 4-(piperidinoalkyl)-3,5-dioxomorpholine.methanesulfonates are prepared as follows:

4-[5-(2-Benzhydrylpiperidino)pentyl]-3,5-dioxomorpholine.methanesulfonate by the following sequence of steps: (a) by reacting diglycolic anhydride and 5-aminopentanol to produce [2-(5-hydroxypentyl)amino-2-oxoethoxy]acetic acid, (b) heating to cyclize the latter to obtain 4-(5-hydroxypentyl)-b 3,5-dioxomorpholine, (c) esterifying the latter with methanesulfonyl chloride to produce 5-(3,5-dioxomorpholino)pentyl methanesulfonate and (d) reacting the mesylate with 2-benzhydrylpiperidine.

4-[2-(4-Bis(2-bromo-p-tolyl)methyl)piperidino)-propyl]-3,5-dioxomorpholine.methanesulfonate by (a) reacting diglycolic anhydride and 3-aminopropanol to produce [2-(3-hydroxypropyl)amino-2-oxoethoxy]acetic acid, (b) heating to cyclize the latter to obtain 4-(3-hydroxypropyl)-3,5-dioxomorpholine, (c) esterifying the latter with methanesulfonyl chloride to produce 3-(3,5-dioxomorpholino)propyl methanesulfonate and (d) reacting the mesylate with 4-[bis(2-bromo-p-tolyl)methyl]piperidine.

4-{4-[3-(Bis(4-butoxy-o-tolyl)methyl]piperidino)-butyl}-3,5-dioxomorpholine.methanesulfonate by (a) reacting diglycolic anhydride and 4-aminobutanol to produce [2-(4-hydroxybutyl)amino-2-oxoethoxy]acetic acid, (b) heating to cyclize the latter to obtain 4-(4-hydroxybutyl)-3,5-dioxomorpholine, (c) esterifying the latter with methanesulfonyl chloride to produce 4-(3,5-dioxomorpholino)butyl methanesulfonate and (d) reacting the mesylate with 3-[bis(4-butoxy-o-tolyl)methyl]piperidine.

4-(2-Piperidinoethyl)-3,5-dioxomorpholine.methanesulfonate by (a) reacting diglycolic anhydride and 2-aminoethanol to produce [2-(2-hydroxyethylamino)-2-oxoethoxy]acetic acid, (b) heating to cyclixe the latter to obtain 4-(2-hydroxyethyl)-3,5-dioxomorpholine, (c) esterifying the latter with methanesulfonyl chloride to produce 2-(3,5-dioxomorpholino)ethyl methanesulfonate and (d) reacting the mesylate with piperidine.

EXAMPLE XVII

Employing starting materials described in Example XVI are procedures similar to that described in Examples XIII, the following salts are prepared:

Sodium {2-[5-(2-benzhydrylpiperidino)pentylamino]-2-oxoethoxy}acetate by the reaction of 4-[5-(2-benzhydrylpiperidino)pentyl]-3,5-dioxomorpholine.methanesulfonate and sodium hydroxide.

Tetrabutylammonium {2-3-(3-(4-(bis(2-bromo-p-tolyl)-methyl)piperidino)propylamino]-2-oxoethoxy-}acetate by the reaction of 4-{3-[4-bis(2-bromo-p-tolyl)-methyl)piperidino]-propyl}-3,5-dioxomorpholine.methanesulfonate and tetrabutylammonium hydroxide.

Tetramethylammonium {2-[4-(3-bis(4-n-butoxy-o-tolyl)-methyl)piperidino)butylamino]-2-oxoethoxy}acetate by the reaction of 4-{4-[3-(bis(4-n-butoxy-o-tolyl)- methyl)piperidino]-butyl}-3,5-dioxomorpholine.methanesulfonate and tetramethylammonium hydroxide.

Calcium {2-[2-piperidinoethylamino]-2-oxoethoxy}acetate by the reaction of 4-[2-piperidinoethyl]-2,4-dioxomorpholine.methanesulfonate and calcium hydroxide.

EXAMPLE XVIII

{2-[6-(4-Benzhydrylpiperidino)hexyl]amino-2-oxoethoxy}acetic Acid

A 1.02 gram (2.10 millimoles) sample of sodium {2-[6-(4-benzhydrylpiperidino)hexyl]amino-2-oxoethoxy}acetate (prepared as described in Example XIII) and 7.3 milliliters of 5 N aqueous NaOH is heated under reflux temperature for 1.5 hours to obtain 6-piperidinohexamine and diglycolate in the reaction mixture; the mixture is then diluted with 25 milliliters of water and extracted with ether. The ether solution is washed with aqueous NaCl, dried with $Na_2SO_4$, and concentrated to obtain as residue, 6-piperidinohexamine. To a solution of 0.685 grams (1.96 millimoles) of the thus prepared 6-piperidinohexamine in 14 milliliters of dichloromethane is added drop by drop during about 10 minutes, a warm solution of 0.227 (1.95 millimole) of diglycolic anhydride in 26 ml. of dichloromethane. After the addition, the mixture is stirred at a temperature range of 25°–30° C. for two hours to obtain the desired {2-[6-(4-benzhydrylpiperidino)hexyl]amino-2-oxoethoxy}acetic acid; the latter is isolated by volatilization of the solvent.

EXAMPLE XIX

{2-[6-(4-Benzhydrylpiperidino)hexyl]amino-2-oxoethoxy}acetic acid.1-naphthalene sulfonate To a solution of 0.100 grams (0.215 millimole) of {2-[6-(4-benzhydrylpiperidino)hexyl]amino-2-oxoethoxy}acetic acid in ethanol is added 0.056 grams (0.22 millimole) of 1-naphthalenesulfonic acid dihydrate. After thorough mixing followed by volatilization of the solvent there is left as residue the desired {2-[6-(4-benzhydrylpiperidino)hexyl]amino-2-oxoethoxy}acetic acid.1-naphthalene sulfonate.

EXAMPLE XX

The following acid addition salts may be prepared from the appropriate morpholinediones in the free base form, said morpholinediones having been prepared as described as the second step in Example IX or the first step in Example X, thereafter preparing the salt in a manner similar to that described in Example XIII, and then following procedures similar to those described in Examples XVIII and XIX:

[2-(6-Piperidinohexyl)amino-2-oxoethoxy]acetic acid.picrate.
[2-(6-Piperidinohexyl)amino-2-oxoethoxy]acetic acid.methanesulfonate.
{2-[3-(4-Bis(2-bromo-p-tolyl)methyl)piperidino)propyl]amino-2-oxoethoxy}acetic acid.hydrochloride.
{2-[3-(4-(Bis(2-bromo-p-tolyl)methyl)piperidino)propyl]amino-2-oxoethoxy}acetic acid.ethanesulfonate.
{2-[2-(4-Benzhydrylpiperidino)ethyl]amino-2-oxoethoxy}acetic acid.hydrobromide.
{2-[2-(4-Benzhydrylpiperidino)ethyl]amino-2-oxoethoxy}acetic acid.hydrogen sulfate.
{2-[4-(3-(Bis(4-butoxy-o-tolyl)methyl)piperidino)butyl]amino-2-oxoethoxy}acetic acid.hydroiodide.
{2-[4-(3-Bis(4-butoxy-o-tolyl)methyl)piperidino)butyl]amino-2-oxoethoxy)acetic acid.phosphate.

EXAMPLE XXI

The following amide acids may be prepared employing procedure similar to that described in Example XVIII.

{2-(6-Piperidinohexyl)amino-2-oxoethoxy}acetic acid.
{2-[3-(4-(Bis(2-bromo-p-tolyl)methyl)piperidino)propyl]amino-2-oxoethoxy}acetic acid.
{2-[2-(4-Benzhydrylpiperidino)ethyl]amino-2-oxoethoxy}acetic acid.
{2-[4-(3-(Bis(4-butoxy-o-tolyl)methyl)piperidino)butyl]amino-2-oxoethoxy}acetic acid.

EXAMPLE XXII

The following salts of amide acids (prepared as described in Example I, II and V) may be obtained by intimately contacting the acid with a substantially equivalent amount of the appropriate amine or aqueous base:

Potassium {2-[(2-Cyclohexyl-1-methylethyl)methylamino]-2-oxoethoxy}acetate.
Calcium {2-[(2-Cyclohexyl-1-methylethyl)methylamino]-2-oxoethoxy}acetate.
Ammonium {2[(2-Cyclohexyl-1-methylethyl)methylamino]-2-oxoethoxy}acetate.
Isopropylammonium {2-[(2-Cyclohexyl-1-methylethyl)methylamino]-2-oxoethoxy}acetate.
Sodium [2-(1-adamantylamino)-2-oxoethoxy]acetate.
Magnesium [2-(1-adamantylamino)-2-oxoethoxy]acetate.
Tris(2-hydroxyethyl)ammonium [2-(1-adamantylamino)-2-oxoethoxy]acetate.
Tetraethylammonium [2-(4-benzhydrylpiperidino)-2-oxoethoxy]acetate.
Isoamylammonium [2-(4-benzhydrylpiperidino)-2-oxoethoxy]acetate.
Sodium [2-(4-benzhydrylpiperidino)-2-oxoethoxy]acetate.
Bis(2-hydroxyethyl)ammonium [2-(4-benzhydrylpiperidino)-2-oxoethoxy]acetate.
2-Hydroxypropylammonium [2-(4-benzhydrylpiperidino)-2-oxoethoxy]acetate.

EXAMPLE XXIII

In a manner similar to that described in Example XIII, the following morpholine bases are obtained from the acid addition salt by treating a chloroform or dichloromethane solution of the acid addition salt with dilute aqueous sodium hydroxide, separating the halohydrocarbon solution, vaporizing the solvent and recovering as residue:

4-[6-(4-Benzhydrylpiperidino)hexyl]-3,5-dioxomorpholine.
4-[6-(4-Di-p-tolylmethyl)piperidino]hexyl)-3,5-dioxomorpholine.
4-{6-[4-(Bis(p-methoxyphenyl)methyl)piperidino]-hexyl}-3,5-dioxomorpholine.
4-{6-[4-(Bis(p-chlorophenyl)methyl)piperidino]hexyl}-3,5-dioxomorpholine.

EXAMPLE XXIV

In a manner similar to that described in Example III and IV, the following compounds may be prepared:

{2-Oxo-2-[methyl-2-(p-trifluoromethylphenyl)e-thylamino]ethoxy}acetic acid.

{2-Oxo-2-[propyl-2-(p-tolyl)ethylamino]-ethoxy}acetic acid.

{2-Oxo-2-[ethyl-2-(p-chlorophenyl)ethyl-amino]ethoxy}acetic acid.

EXAMPLE XXV

Employing procedures similar to that described in the foregoing examples, the following compounds may be prepared:

{2-{4-[(4-Ethoxyphenyl)phenylmethyl]-piperidino}-2-oxoethoxy}acetic acid.

{2-{3-[(4-Chlorophenyl)phenylmethyl]-piperidino}-2-oxoethoxy}acetic acid.

{2-{2-[(4-Ethylphenyl)phenylmethyl]-piperidino}-2-oxoethoxy}acetic acid.

{2-{3{3-[(4-Chlorophenyl)phenylmethyl]-piperidino}propyl}amino-2-oxoethoxy}acetic acid.

{2-{5-{3-[(p-Tolyl)phenylmethyl]-piperidino}pentyl}amino-2-oxoethoxy}acetic acid.

{2-{2-{3-[(4-Methoxyphenyl)phenylmethyl]-piperidino}ethyl}amino-2-oxoethoxy}-acetic acid.

Potassium {2-{4-[(4-Ethoxyphenyl)-phenylmethyl]-piperidino}-2-oxoethoxy}acetate.

Calcium {2-{3-[(4-chlorophenyl)-phenylmethyl]-piperidino}-2-oxoethoxy}acetate.

t-Butylammonium {2-{2-[(4-ethylphenyl)phenylmethyl]piperidino}-2-oxoethoxy}acetate.

Tetramethylammonium {2-{3-{3-[(4-chlorophenyl)-phenylmethyl]piperidino}propyl}-amino-2-oxoethoxy}acetate.

Magnesium {2-{5-{3-[(p-Tolyl)-phenylmethyl]-piperidino}pentyl}amino-2-oxoethoxy}acetate.

Tetrabutylammonium {2-{2-{3-[(4-Methoxyphenyl)phenylmethyl]piperidino}-ethyl}-amino-2-oxoethoxy}acetate.

The starting materials for the preparation of the morpholinediones and/or the amide acids of the present invention as previously described are either readily available or known materials, or may be prepared by methods described in the literature. Diglycolic anhydride, amino alcohols and the amines represented by the structures

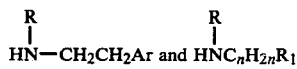

are generally known compounds.

The secondary amines may be prepared by conventional alkylation of a primary amine. Of the amines represented by the formula

those in which $R_2$ is a simple cycloalkyl group and R is hydrogen are known amines; those in which $R_2$ is a simple cyclohexyl and R is an alkyl group, are generally known and may be prepared employing conventional alkylation procedures from the known cycloalkylamine. When $R_2$ is a condensed cycloalkyl group, the known amines are adamantylamine, norbornanylamine and bornanylamine. The diarylmethylpiperidines represented by the formula

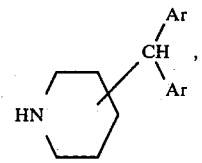

may be prepared by the reduction of the corresponding diarylmethylpyridines employing methods such as hydrogenation in the presence of platinum oxide, Raney-Nickel or palladium on charcoal catalyst. The hydrogenation is described in numerous places in the literature such as in the article by E. Sury et al, Helv. Chim. Acta., 248, 2133 (1954), or R. W. Hamilton et al, U.S. patent 3,267,108 (Chemical Abstracts 65, 15347 $^{e\text{-}g}$). The diarylmethylpyridine compounds which are to be hydrogenated may be prepared in several ways by established procedures. Many of these compounds are well known compounds. One of the methods for preparing the diarylpyridine compound is by reacting an appropriate bromopyridine and diarylacetonitrile in the presence of sodamide, followed by the hydrolysis of the nitrile group with concentrated sulfuric acid or concentrated base and thereafter decarboxylating the resulting carboxyl group. Alternatively, the diarylmethylpyridine compounds may be prepared through a diarylpyridylcarbinol followed by the reduction of the carbinol hydroxyl group to a hydrocarbon group with palladium on charcoal. One method for preparing the diarylpyridylcarbinol is by the Grignard synthesis employing an aroylpyridine and arylmagnesium bromide followed by hydrolysis of the Grignard complex employing conventional procedures. The diarylpyridylcarbinol may also be prepared by the reaction of pyridyl lithium with an appropriate diaryl ketone to obtain the diarylpyridylcarbinol. Another method reported in the aforementioned U.S. Pat. No. 3,267,108 is the reaction of an aroyelpyridine and arylmagnesium bromide which on hydrolysis produces a diarylpyridylcarbinol which is then reduced with hydrogen iodide and sodium bisulfite to obtain the desired diarylmethylpyridine. Still other methods for preparing diarylpyridylmethane are reported in U.S. Pat. No. 3,397,273. One of these is the reaction of two moles of benzene or a substituted benzene with pyridylcarboxaldehyde in the presence of concentrated sulfuric acid to obtain a pyridyldiarylmethane which is readily isolated from the reaction mixture by conventional extraction procedures. Another method employs heating diarylpyridinemethanol in a mixture of glacial acetic acid, concentrated hydrochloric acid and 47 percent aqueous hydroiodic acid to reduce the hydroxyl group.

What is claimed is:

1. A compound represented by the formula

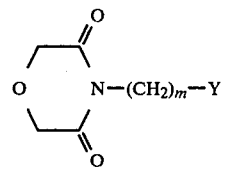

wherein Y is a piperidine or substituted piperidine radical represented by wherein

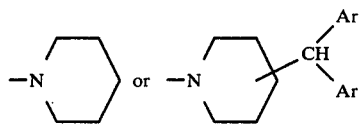

each Ar independently is phenyl, trifluoromethylphenyl, halo-substituted-phenyl, lower alkyl-substituted-phenyl or lower alkoxy-substituted-phenyl;

m is an integer of from 2 to 6; and acid addition salts.

2. A compound according to claim 1 which is 4-[6-(4-Benzhydrylpiperidino)hexyl]-3,5-dioxomorpholine.

3. A compound according to claim 1 which is 4-(6-piperidinohexyl)-3,5-dioxomorpholine.

* * * * *